(12) United States Patent
Nitsch et al.

(10) Patent No.: US 7,973,547 B2
(45) Date of Patent: Jul. 5, 2011

(54) METHOD AND APPARATUS FOR DETECTING A CRACK IN A SEMICONDUCTOR WAFER, AND A WAFER CHUCK

(75) Inventors: Alois Nitsch, Munich (DE); Rainer Tilgner, Munich (DE); Horst Baumeister, Munich (DE)

(73) Assignee: Infineon Technologies AG, Neubiberg (DE)

( * ) Notice: Subject to any disclaimer, the term of this patent is extended or adjusted under 35 U.S.C. 154(b) by 253 days.

(21) Appl. No.: 12/190,745

(22) Filed: Aug. 13, 2008

(65) Prior Publication Data

US 2010/0039128 A1    Feb. 18, 2010

(51) Int. Cl.
*G01R 31/308* (2006.01)
(52) U.S. Cl. .................................. 324/754.25
(58) Field of Classification Search ........... 324/158.1, 324/760–765; 438/14–18
See application file for complete search history.

(56) References Cited

U.S. PATENT DOCUMENTS

| | | | |
|---|---|---|---|
| 4,513,384 A | | 4/1985 | Rosencwaig |
| 6,196,062 B1 * | | 3/2001 | Wright et al. ............... 73/105 |
| 6,981,417 B1 * | | 1/2006 | Oravecz ..................... 73/619 |
| 2008/0177258 A1 * | | 7/2008 | Govari et al. ............... 606/41 |
| 2009/0272191 A1 * | | 11/2009 | Maris et al. ................ 73/618 |

FOREIGN PATENT DOCUMENTS

EP    1 855 107 A1    11/2007

OTHER PUBLICATIONS

Tilgner, R., et al., "Changing States of Delamination Between Molding Compound and Chip Surface: A Challenge for Scanning Acoustic Microscopy," IEEE Transactions on Components and Manufacturing Technology—Part B, Aug. 1994, pp. 442-448, vol. 17, No. 3, IEEE.
"Mechanical Characterization Lab. Nanoindentation—Micro Scratch Test—AFM," 2006, 6 pages, Divisione FCS, ITC-irst, Via Sommarive 18, 38050, Povo, Trento, Italy, http://fcs.itc.it/labs/indexPLATFORM.asp.

* cited by examiner

*Primary Examiner* — Ha Tran T Nguyen
*Assistant Examiner* — Trung Q Nguyen
(74) *Attorney, Agent, or Firm* — Slater & Matsil, L.L.P.

(57) ABSTRACT

A method for detecting a crack in a semiconductor wafer, which includes an electrical device and a connecting pad electrically coupled with the electrical device, is described. The crack is detected by an acoustic detector being acoustically coupled to the semiconductor wafer during contacting the contacting pad with a probe.

23 Claims, 4 Drawing Sheets

METHOD AND APPARATUS FOR DETECTING A CRACK IN A SEMICONDUCTOR WAFER, AND A WAFER CHUCK

BACKGROUND

Typically, integrated circuits are produced on wafers and probed or tested on a wafer level before, for example, being diced and shipped as individual integrated circuits or chips. During the production and/or probing of the integrated circuits at wafer level, cracks within the wafer may be created due to mechanical stress or thermo-mechanical stress. These cracks may, for example, create short circuits or leakage currents within individual integrated circuits of the wafer.

SUMMARY OF THE INVENTION

Embodiments of the invention allow the detection of cracks created during probing of integrated circuits at wafer level. Acoustic sensors or detectors are acoustically coupled to the wafer, and receive, in case a crack is created during the probing, the respective acoustic crack signal at the instant that the crack is produced in the wafer.

Thus, in-situ crack detection and immediate reactions to the detection of such cracks is possible.

The acoustic sensors for detecting the crack, can, for example, be located at or integrated into a wafer chuck, into which the wafer is mounted, or into or at a probe of a wafer probing apparatus.

BRIEF DESCRIPTION OF THE DRAWINGS

Embodiments of the present invention are described hereinafter making reference to the appended drawings.

DETAILED DESCRIPTION OF ILLUSTRATIVE EMBODIMENTS

Figure 1:
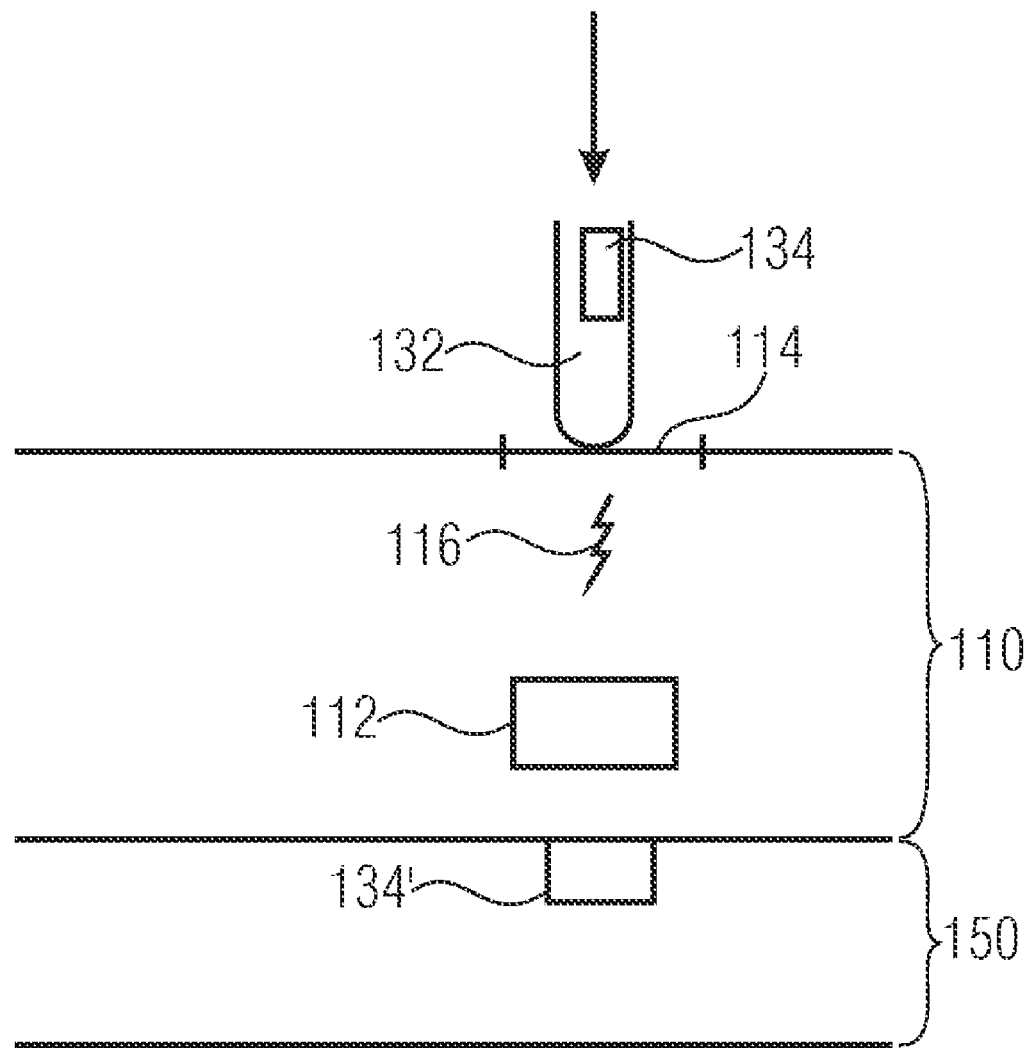
FIG. 1 shows a schematic diagram of two embodiments for arranging an acoustic detector or acoustic sensor (wafer chuck and probe) of an apparatus for detecting a crack in a semiconductor wafer.

Equal or equivalent elements are denoted in the following description of the figures by equal or equivalent reference numerals.

FIG. 1 shows a schematic diagram of an apparatus for detecting a crack 116 in a semiconductor wafer 110, the semiconductor wafer 110 comprising an electrical device 112 and a connecting pad 114, which is electrically coupled (not shown) with the electrical device 112. The apparatus for detecting a crack comprises a probe 132, which is adapted to mechanically or physically contact the connecting pad 114 of the semiconductor wafer 110. The probe 132 is typically used to electrically connect electrical devices or circuits integrated in the semiconductor wafer 110, for example, the electrical device 112, to perform electrical or functional tests.

The embodiment of the apparatus further comprises an acoustic sensor or acoustic detector 134, 134', which is acoustically coupled to the semiconductor wafer.

The crack 116 may, for example, be produced when the probe 132 is moved down (see arrow), thus generating a mechanical stress or pressure on the part of the semiconductor wafer below the connecting pad 114. This mechanical stress may, as previously explained, produce cracks anywhere in the semiconductor wafer, typically within the part below the connecting pad 114. The cracks themselves can propagate vertically (as shown in FIG. 1) or angularly.

When this crack is produced, a specific or characteristic acoustic signal, the "acoustic crack signal", is generated, which is propagated in form of acoustic waves through the semiconductor wafer 110, and can be measured by the acoustic sensor or acoustic detector 134, 134', which is acoustically coupled to the semiconductor wafer 110.

The acoustic detector 134, 134' is adapted to detect the crack 116 based on the acoustic crack signal produced when the probe 132 is in mechanical contact with the connecting pad 114, or in other words, at the time the probe 132 contacts the connecting pad 114.

Embodiments of the acoustic detector 134, 134' comprise basically two functional units: an acoustic sensor 134, 134' and a crack detection unit (not shown). These two functional units may be integrated into one device, forming an integrated acoustic detector 134, 134', or may be implemented as two separate devices.

In order to avoid unnecessary repetitions like "acoustic sensor and acoustic detector 134, 134'", in the following it will be referred to the acoustic sensor 134, 134'. However, it should be kept in mind that, unless otherwise stated, the explanations with regard to the acoustic sensor 134, 134', in particular with regard to the position of the acoustic sensor, also apply to the integrated acoustic detector 134, 134'.

The acoustic sensor 134, 134' senses and converts the acoustic crack signal into, for example, a corresponding "electric crack signal" and transmits the corresponding electric crack signal to the crack detection unit, which then detects the creation of the crack.

In further embodiments comprising an acoustic sensor and a crack detection unit, the acoustic sensor can be adapted to perform a different signal conversion, for example, an electric to optic signal conversion and transmit an "optical crack signal" to the crack detection unit.

Embodiments comprising one or a plurality of acoustic sensors and a separate crack detection unit allow for the use of standard acoustic sensors, which keep the cost low.

In embodiments of the apparatus for detecting, the detection of the crack may be performed using specific crack detection signal processing, which allows the distinguishing of the acoustic or electric crack signal from other acoustic signals.

FIG. 1 shows two possible embodiments for arranging the acoustic sensor 134, 134'.

According to a first embodiment, the acoustic sensor 134 is integrated in the probe and acoustically coupled to the probe, and via the probe 132 to the wafer 110. In alternative embodiments, the acoustic sensor 134 can also be arranged at the circumference of the probe 132.

In a second embodiment of the apparatus for detecting the crack, the latter comprises a wafer chuck 150, on which the semiconductor wafer 110 is mounted, and into which the acoustic sensor 134' is integrated. The acoustic sensor 134' is acoustically coupled to the wafer chuck 150 and via the wafer chuck 150 to the wafer 110, or directly coupled to the wafer 110. In further embodiments, the acoustic sensor 134' can be arranged at the circumference of the wafer chuck, for example, on the side surfaces of the wafer chuck 150, or at the bottom surface of the wafer chuck 150.

The substrate 110 can for instance be a silicon substrate or any other semiconductor substrate.

The acoustic sensor 134, 134' can for instance be a piezoelectric sensor or any other sensor capable of detecting the acoustic crack signal.

Figure 2A:
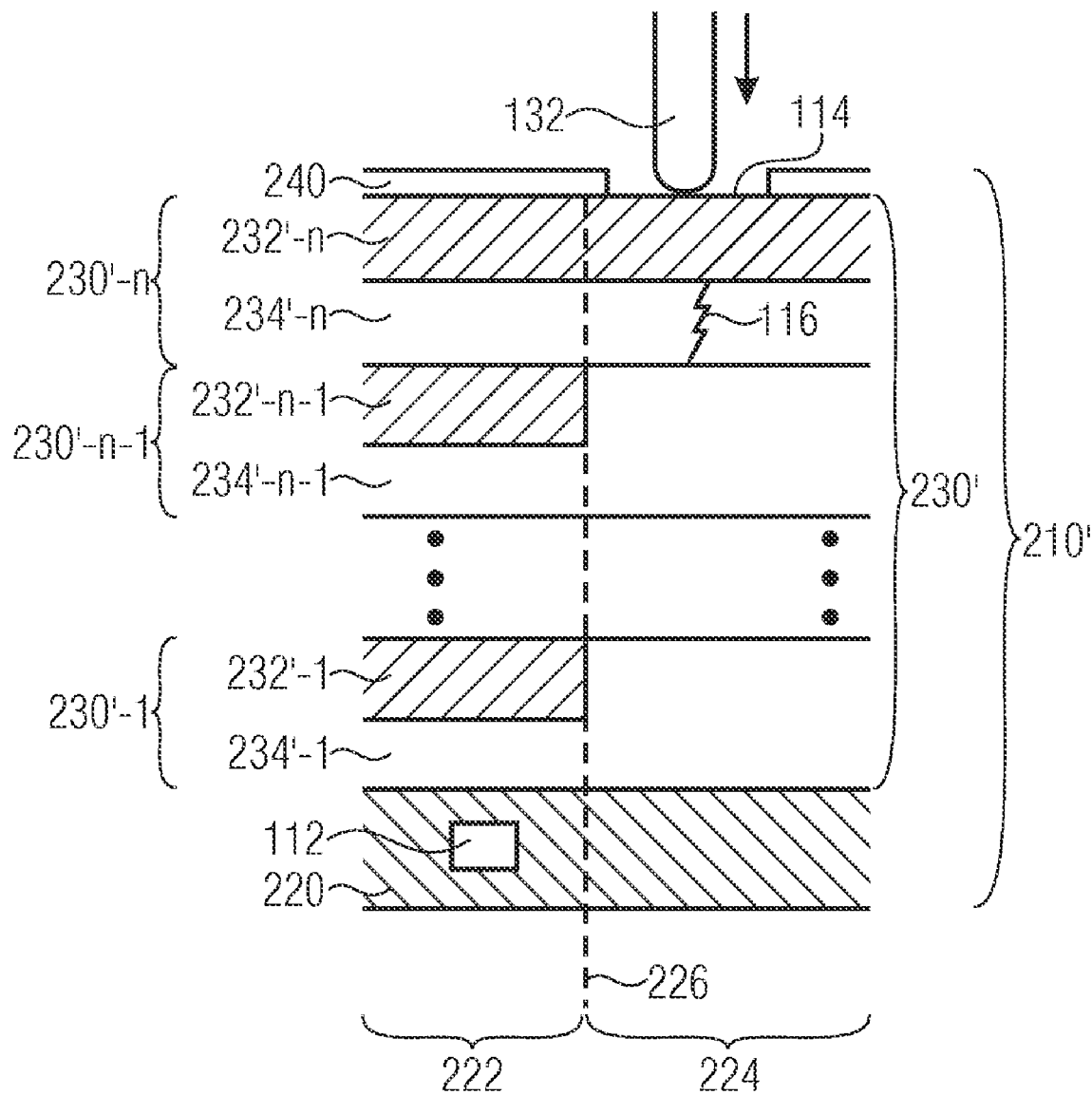
FIG. 2A shows a schematic diagram of a wafer with a conventional connecting pad arrangement.

FIG. 2A shows a semiconductor wafer 210' comprising a semiconductor substrate 220, on which a stack 230' of connecting layers is arranged. The stack of connecting layers 230' comprises n layers of connecting layers 230'-1 to 230'-n, wherein the reference number 230'-1 refers to the first conductive layer arranged on top of the semiconductor substrate 220 and wherein the reference number 230'-n refers to the uppermost connecting layer of the stack of connecting layers 230'. On top of the uppermost connecting layer 230'-n a passivation layer 240 is arranged to protect and electrically insulate the wafer and electrical structures below the passivation layer 240. At certain positions, openings in the passivation layer 240 are created as connecting pads 114.

As shown in FIG. 2A, the connecting layer 230'-1 can comprise a metal layer 232'-1, arranged on top of a dielectric layer 234'-1. The same reference numbering scheme also applies to the other connecting layers 230'-2 (not shown) to 230'-n. According to the embodiment shown in FIG. 2A, the dielectric layer 234'-1 electrically insulates the metal layer 232'-1 from the semiconductor substrate 220, whereas the dielectric layers 234'-2 to 234'-insulate the respective metal layers 232'-2 to 232'-n from other layers 230'-1 to 230'-n-1 arranged below the respective connecting layer 230'-2 to 230'-n.

Further embodiments of the semiconductor wafer may comprise different structures of connecting layers.

The wafer 210' as shown in FIG. 2A comprises two areas, a first substrate area 222 and a second substrate area 224 which are separated by a borderline 226. Within the first substrate area 222, at least one electrical device 112 is integrated in the substrate 220. The electrical device 112 can be a diode, transistor, or any other active integrated electrical device, or an integrated resistor, capacitor or inductor, or any other integrated passive element. In further embodiments, the electrical element 112 is part of an integrated circuit comprising a plurality of electrical devices. Therefore, the first substrate area is also referred to as "active area" or "active chip area". In contrast thereto, the second substrate area 224 typically does not comprise any electrical devices, and is also referred to as "inactive area" or "inactive chip area".

Figure 2B:
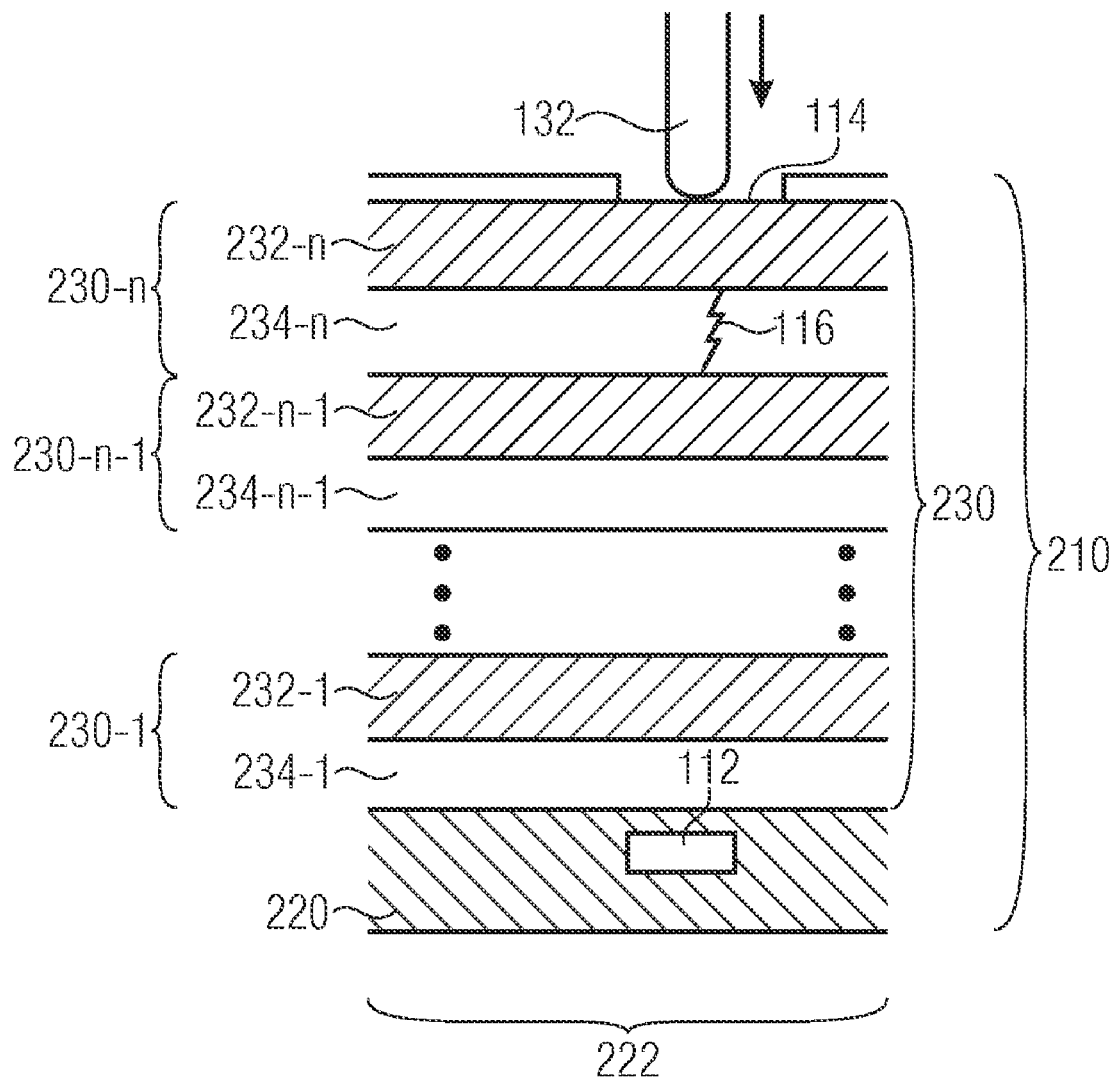
FIG. 2B shows a schematic diagram of a wafer with a connecting pad arranged above the active area of the chip.

As can be seen from FIG. 2A, the connecting layers 230'-1 to 230'-n are arranged above the first substrate area 222 and the connecting pad 114 is arranged above the second substrate area 224. This structure is also referred to as a standard design or standard pad design FIG. 2B shows a semiconductor wafer 210 with a semiconductor substrate 220 and a layer stack 230 comprising n layers of connecting layers 230-1 to 230-n. In contrast to FIG. 2A, FIG. 2B shows an embodiment of a semiconductor wafer, where the connecting pad 114 is arranged above the first substrate area or active chip area 222, and wherein the metal layers 232-1 to 232-n of the conducting layers 230-1 to 230-n extend below the connecting pad 114.

In the embodiment according to FIG. 2B the total wafer and substrate area is more efficiently used than in the embodiment according to FIG. 2A, as the second substrate area or inactive chip area 224 can be reduced, or even completely avoided, by placing the connecting pad 114 above the active chip area 222.

On the other hand, for embodiments according to FIG. 2B, the risk of cracks leading to short circuits or leakage currents is higher than for embodiments according to FIG. 2A.

The standard pad design according to FIG. 2A reduces the risk of the creation of short circuits or leakage currents when the probe 132 is moved down (see arrow) to contact the connecting pad 114, as no pressure sensitive electrical device 112 is arranged below the connecting pad 114. Furthermore, only the metal layer 232'-n of the upmost connecting layer 230'-n extends above the second substrate area 224 to provide the electrical connecting with the connecting pad 114. Therefore, even if the mechanical stress caused by the probe 132 produces a crack 116 within the dielectric layer 234'-n, electrical failures such as a short circuit generation or leakage current generation is prevented.

In embodiments according to FIG. 2B, an electrical device 112 or even a plurality of electrical devices or elements of an integrated circuit are arranged below the connecting pad 114 and may be damaged by a crack generation, because of the mechanical stress applied to them by the probe 132 during wafer probing. Furthermore, the mechanical stress generated by the probe 132 when moved down to connect to the connecting pad 114 (see arrow) may produce a crack, for example, in the dielectric layer 234-n and short circuit the metal layer 232-n and the metal layer 232-n-1, in other words, short circuit neighboring metal layers.

Figure 3:
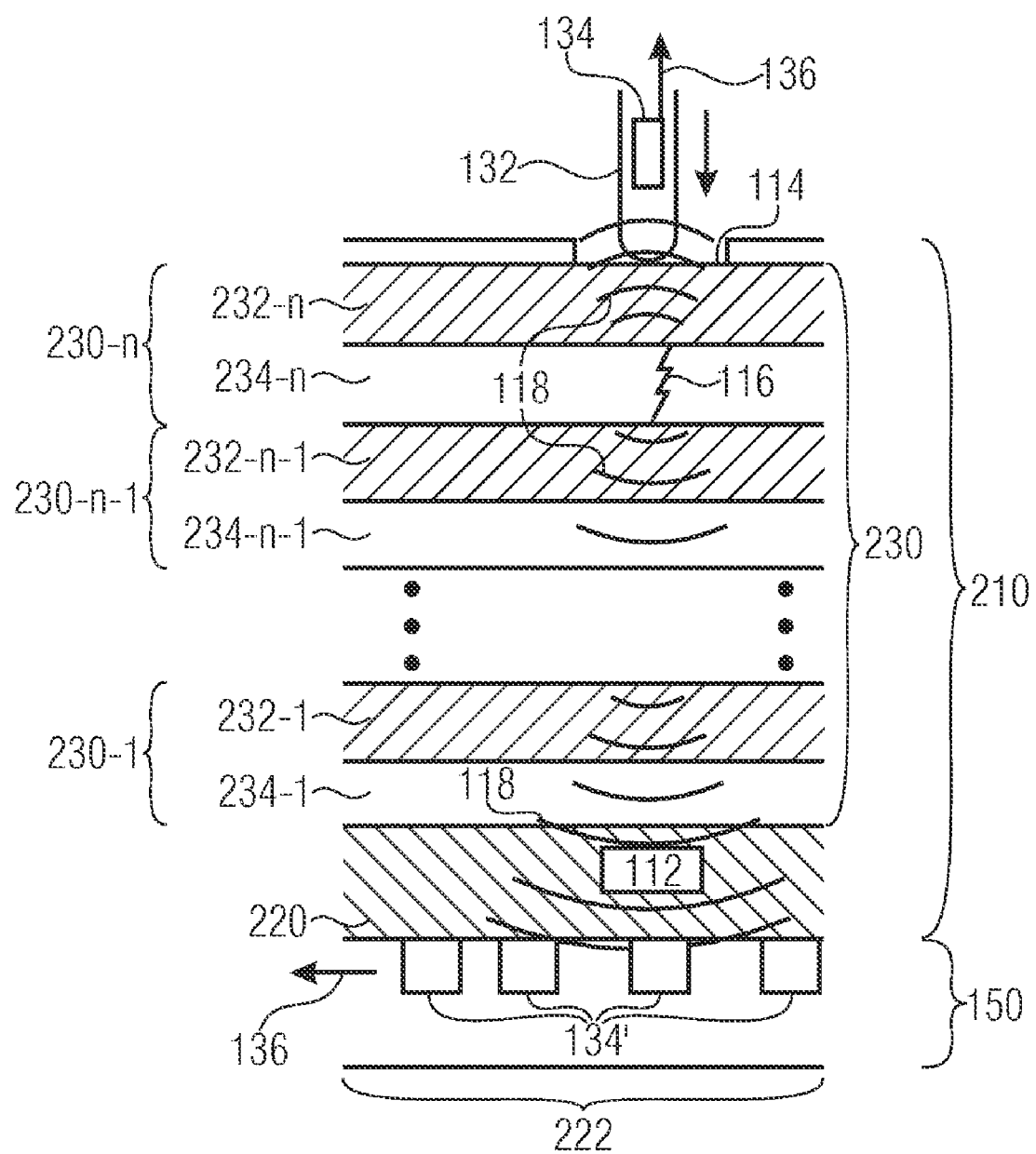
FIG. 3 shows a schematic diagram of two embodiments for arranging an acoustic detector or acoustic sensor (wafer chuck and probe) of an apparatus for detecting a crack in a semiconductor wafer during the probing of a wafer with a semiconductor substrate and a layer stack.

FIG. 3 shows an embodiment of an apparatus for detecting a crack in a semiconductor wafer according to FIG. 2B. In addition to FIG. 2B, FIG. 3 shows the acoustic crack signal 118 (shown as wave front) propagating through the connecting layers 230-1 to 230-n to the acoustic sensor 134, 134', as already described based on FIG. 1. Like FIG. 1, FIG. 3 shows two embodiments of the apparatus for detecting a crack 116. The first embodiment comprises the acoustic sensor 134 integrated in the probe 132, and the second embodiment comprises a sensor 134' integrated into the wafer chuck 150. FIG. 3 shows a further embodiment, where the acoustic sensor 134, 134' converts the acoustic crack signal 118 into an electric crack signal 136, which are for instance read out from the acoustic sensors 134, 134' to a crack detection unit or read out unit (not shown).

No additional coupling medium between wafer or medium back side and the wafer chuck is needed. Punctual mechanic contact between wafer back side and chuck is sufficient for coupling an acoustic signal from the wafer into the chuck.

The sensor surface should have an acoustic impedance which is as similar as possible to the acoustic impedance of the semiconductor wafer, for instance, a silicon wafer.

Any type of an acoustic sensor or detector, for example, a piezocrystal with sufficient sensitivity, may be placed either in the wafer chuck of the test system or in the probe pad, as shown in FIG. 3.

Embodiments of the apparatus for detecting a crack 116, can comprise one acoustic sensor 134, 134', or a plurality of acoustic sensors 134 or 134'. FIG. 3 exemplarily shows the plurality of acoustic sensors 134'. The acoustic sensors 134' can be arranged in a matrix-like manner or other patterns.

The use of a plurality of acoustic sensors 134, 134' could allow additionally for a localization of the crack.

Embodiments of the crack detection unit or readout system distinguish between acoustic signals due to the chuck movement or other system vibration and the crack typical acoustic signal. Therefore, embodiments of the apparatus for detecting a crack can be implemented to suppress other acoustic signals, e.g., using a filter.

Furthermore, embodiments of the apparatus for detecting a crack can be implemented to detect the crack 116, based on a threshold evaluation, i.e., detect a crack 116, when the magnitude of the acoustic crack signal is higher than a certain threshold.

Other embodiments can be implemented to apply, for instance, known pattern recognition methods, i.e., comparing the acoustic crack signal or its electric equivalent with known reference crack signals, for example, in the frequency domain, and detect a crack 116 in case the received crack acoustic crack signal matches to a reference acoustic crack signal or its electric equivalent.

The larger the distance between the position of the crack 116 and the acoustic sensor 134, 134', the more attenuated the acoustic crack signal becomes. Therefore, acoustic sensors 134 integrated in the probes 132 or acoustic sensors 134' integrated into the wafer chuck 150 directly below a connecting pad 114, allow for the detection of "smaller cracks", or in other words, the detection of acoustic crack signals with a lower magnitude.

The respective thresholds and/or reference acoustic crack signals can, for example, be determined by performing a priori tests simulating the production or probing environment for different pressures applied to the connecting pads 14 and measuring the respective acoustic crack signals and/or their magnitudes for the one or the plurality of acoustic sensors as they will be used during for instance mass production and/or mass probing.

In contrast to known systems and methods using scanning acoustic microscopy (SAM), embodiments of the apparatus and the method for detecting a crack do not need to comprise an ultrasonic source. Embodiments of the method and the apparatus can only rely on an acoustic signal produced when the wafer cracks.

An embodiment of a method for detecting a crack 116 in a semiconductor wafer 110, 210, 210' comprises an electrical device 112 and a connecting pad 114 electrically coupled with the electrical device 112, comprises: detecting the crack 116 by an acoustic detector 134, 134' being acoustically coupled to the semiconductor wafer 110, 210, 210' during contacting the connecting pad 114 with a probe 132.

The method can be part of a method for probing a semiconductor wafer during or after the manufacturing of the semiconductor wafer. In embodiments of the method for probing or detecting the probe is moved towards the wafer to mechanically and electrically contact the probe with the connecting pad 114

Referring to the aforementioned explanations and as can be seen from FIGS. 2A and 2B, compared to the standard design of FIG. 2A, the connection pads 114 of the design according to FIG. 2B are shifted to positions above the active chip area 222. This results in less mechanical stability, compared with the standard pad, as shown in FIG. 2A.

A crack 116 in one or more dielectric layers 234-1 to 234-*n* also referred to as inter-metal dielectric (IMD) may cause an unintended electrical leakage current which leads to malfunction of the integrated circuit.

Electrical methods for accelerated electrical activation of cracks in dielectric layers are available. For instance, high temperature operating live tests (HTOL) are usually applied to a certain number of devices prior to mass production. These tests are also used, for example, to adapt the production parameters to achieve a certain target failure rate. From the electrical results, i.e., the leakage current, a potential failure rate is calculated for the product respectively the mass production. However, if after a successful qualification the probing conditions or the mechanical stability of the integrated circuit runs out of specification, unseen or unrecognized, the cracks could lead to fails at the customer site. Furthermore, acceleration tests such as HTOL are not applicable for productive volumes, i.e., for mass production.

Embodiments of the method and apparatus use an acoustic signal, which is sent out, similar to an acoustic emission (AE), during the damaging of a dielectric layer. The acoustic signal propagates all over the wafer and is detectable with sensitive acoustic signal transducers as for instance piezo-cells which are attached, either to the wafer back side, for example, mounted in a wafer chuck, or mounted on the inside of a probe cart or probe head.

In other words, embodiments of the method and the apparatus provide an in situ detection of crack generation during the probing process by detecting the acoustical crack signal and can be used, for example, as "in situ detection of layer damages due to mechanical overstress of layer stacks during wafer probing".

A system, for example, an array of acoustic sensors can be located either in the wafer chuck of a probing system or in the probe pad. The probing process may be automatically stopped if any crack occurrence is detected by the acoustic emission signal (AES) read out system.

Further embodiments are a probing apparatus comprising an embodiment of an apparatus for detecting a crack in a semiconductor wafer, wherein the probe is mechanically contacted and electrically connected with the connecting pad 114 to perform electrical or functional tests for one or more electrical devices 112 or for integrated circuits comprising one or more electrical devices 112.

Embodiments of the probing apparatus or the apparatus for detecting are implemented to move the probe 132 towards the wafer 110 to mechanically and electrically contact the probe 132 with the connecting pad 114 of the semiconductor wafer 110. To avoid the generation of cracks within the semiconductor wafer due to or during the testing, the probe is moved such that on one hand a good mechanical and electrical contact between the probe 132 and the connecting pad is achieved to ensure reliable electrical testing but on the other hand only a minimum pressure is generated onto the connecting pad and the underlying semiconductor wafer. In case the pressure produced by the probe 132 is to high, for example the probe 132 is moved to far down onto the semiconductor wafer 110 (refer to FIG. 1 or 3), the pressure applied to the semiconductor wafer becomes too high and a crack is generated in the semiconductor wafer.

In other words, the movement of the probe is defined by a parking position, a probing position and the speed with which the probe is moved between these two positions. The probing position is the position, the probe takes for or during the electrical tests, whereas the parking position is the position the probe takes, e.g., between two electrical tests. The diameter of the cone end of the probe, the parking position, the probing position and the speed of the probe may also be referred to as probing parameters or production parameters. These probing parameters together with other production parameters are typically optimized and specified in a pre-phase of a mass production to meet a given target failure rate. This pre-phase is also referred to as production qualification. However, the production or probing conditions may change over time and may lead to the generation of cracks although the probing parameters were originally specified to avoid such crack generation (probing parameters are out of specification).

Therefore, embodiments of the probing apparatus or apparatus for detecting are implemented to stop the probing and/or production of the semiconductor wafers when a crack is detected to avoid the damaging of further semiconductor wafers during probing. After the probing and/or production has been stopped the probing parameters and/or production parameters can be adjusted to again achieve the target failure rate.

In other embodiments, the probing apparatus or apparatus for detecting are implemented to automatically adjust the probing parameters of the semiconductor wafers when a crack is detected to avoid the damaging of further semiconductor wafers during probing. The extent of the adjustment, can, for example, depend on the magnitude of the detected crack signal.

In further embodiments, the apparatus for detecting is implemented to localize the lateral position of the crack 116. Such embodiments may comprise a wafer track 150 with a plurality of acoustic sensors 134' or a plurality of probes 132, which are in contact with their respective connecting pads 114 at the same time, i.e., when the crack is generated. The apparatus for detecting can be implemented to use the acoustic crack signals generated by one or more cracks 116 and received by the plurality of acoustic sensors to determine the lateral position of the one or more cracks 116, based on, for example, triangulation.

Therefore, further embodiments include an apparatus for producing an integrated circuit die or chip, which comprises the probing apparatus or apparatus implemented for detecting a crack during wafer level probing, i.e., before dicing the semiconductor wafer to produce the individual integrated circuit dies or chips. The probing apparatus or apparatus for detecting the crack is implemented to provide at least position information of the crack to determine which integrated circuit die or chip will comprise the crack after dicing the semiconductor wafer. Based on this information, an apparatus for producing an integrated circuit or chip can be implemented, for example, to sort out the respective integrated circuit or chip as being defective. The determination of the defective chip can be based on the lateral position information of the detected crack, e.g., a relative position information with regard to the semiconductor wafer of wafer chuck, in combination with, for example, the layout of the wafer or wafer map, defining where each of the final integrated circuit dies or chips is located with regard to the semiconductor wafer or the wafer chuck.

The defective integrated circuit dies or chips comprising a crack 116 can be treated differently or in a different manner compared to dies or chips which comprise no crack (where no cracks have been detected) and/or which have successfully passed the electrical test. The different treatment can, for example be, performing further tests and/or sorting out the defective semiconductor, whereas the other integrated circuit dies are, e.g., prepared for shipment.

In single-probing embodiments comprising only one probe, the lateral position of the crack and the respective die or chip can be determined based on the known position of the probe.

In parallel-probing embodiments comprising, e.g., 4 or 16 probes, which are used in parallel, the lateral position of the crack(s) and the respective die(s) or chip(s) can be determined based on the known positions of the probes.

In further embodiments, the acoustic sensor 134' can also be implemented in the form of, e.g., a polymer foil with piezoelectric characteristics, which is arranged between the wafer 110 and the wafer chuck 150.

In further embodiments, the mechanical stress can be generated by another object or device than a probe, for example, during wafer bonding or packaging of the semiconductor structure.

Depending on certain implementation requirements of the inventive methods, the inventive methods can be implemented in hardware or in software. The implementation can be performed using a digital storage medium, in particular a disc, CD or a DVD having an electronically readable control signal stored thereon which cooperates with a programmable computer system such that an embodiment of the inventive methods is performed. Generally, an embodiment of the present invention is, therefore, a computer program product with a program code stored on a machine readable carrier, the program code being operative for performing the inventive methods when the computer program product runs on a computer. In other words, embodiments of the inventive methods are therefore a computer program having a program code for performing at least one of the inventive methods when the computer program runs on a computer.

While the aforegoing has been particularly shown and described with reference to particular embodiments thereof, it will be understood by those skilled in the art that various other changes in the form and details may be made without departing from the spirit and scope thereof. It is to be understood that various changes may be made in adapting to different embodiments, without departing from the broader concept disclosed herein and comprehended by the claims that follow.

What is claimed is:

1. A method for detecting a crack in a semiconductor wafer comprising an electrical device and a connecting pad electrically coupled with the electrical device, the method comprising:
    detecting the crack using an acoustic detector that is acoustically coupled to the semiconductor wafer during contacting the connecting pad with a probe, wherein the method is part of a probing process and the probe is contacted with the connecting pad to perform an electrical test of the electrical device, wherein process parameters of the probing process are changed when the crack is detected, wherein the process parameters of the probing process involve at least one of a group consisting of a diameter of a cone end of the probe, a parking position of the probe, probing positions of the probe and a speed of the probe with which the probe is moved between the probing positions.

2. The method according to claim 1, wherein the connecting pad is arranged above the electrical device.

3. The method according to claim 1, wherein the acoustic detector comprises an acoustic sensor that is integrated in or at the probe and is acoustically coupled to the semiconductor wafer during contacting the connecting pad with the probe.

4. The method according to claim 1, wherein the acoustic detector comprises an acoustic sensor that is integrated in or at a wafer chuck on which the semiconductor wafer is mounted, the acoustic sensor being acoustically coupled to the semiconductor wafer during contacting the connecting pad with the probe.

5. The method according to claim 1, wherein the semiconductor wafer comprises a semiconductor substrate and a stack of connecting layers arranged over the semiconductor substrate, and wherein the crack is produced in one of the connecting layers.

6. The method according to claim 1, wherein process parameters of the probing process are changed when the crack is detected or the probing process is stopped when the crack is detected.

7. A method for detecting a crack in a semiconductor wafer comprising an electrical device and a connecting pad electrically coupled with the electrical device, the method comprising:

detecting the crack using an acoustic detector that is acoustically coupled to the semiconductor wafer during contacting the connecting pad with a probe, wherein the semiconductor wafer comprises a semiconductor substrate and a stack of connecting layers arranged over the semiconductor substrate, and wherein the crack is produced in one of the connecting layers, wherein a connecting layer of the stack of connecting layers comprises a metal layer and a dielectric layer for electrically insulating the metal layer from a further metal layer of a further connecting layer of the stack of connecting layers, and wherein the crack is produced in the dielectric layer.

8. A method for detecting a crack in a semiconductor wafer comprising an electrical device and a connecting pad electrically coupled with the electrical device, the method comprising:

detecting the crack using an acoustic detector that is acoustically coupled to the semiconductor wafer during contacting the connecting pad with a probe, wherein the acoustic detector comprises a plurality of acoustic sensors that are acoustically coupled to the semiconductor wafer during contacting the connecting pad with the probe, wherein detecting the crack further comprises:

receiving a crack signal generated during and due to generation of the crack at the plurality of acoustic sensors; and determining a lateral position of the crack based on the crack signal received at the plurality of acoustic sensors.

9. The method according to claim 8, wherein the semiconductor wafer comprises a plurality of integrated circuit dies, the method further comprising:

determining based on the lateral position of the crack a defective integrated circuit die of the plurality of integrated circuit dies, the defective integrated circuit die comprising the crack; and treating the defective integrated circuit die different than other integrated circuit dies that do not comprise a crack.

10. An apparatus for detecting a crack in a semiconductor wafer comprising an electrical device and a connecting pad electrically coupled with the electrical device, the apparatus comprising:

a probe adapted to contact the connecting pad; and an acoustic detector adapted to be acoustically coupled to the semiconductor wafer, wherein the acoustic detector is adapted to detect the crack, wherein the acoustic detector is adapted to detect the crack at the time the probe contacts the connecting pad, and wherein the probe is configured to electrically and mechanically contact the connecting pad, and the apparatus is further configured to perform an electrical and functional test on the electrical device via the probe and the connecting pad.

11. The apparatus according to claim 10, wherein the acoustic detector comprises an acoustic sensor, which is integrated in or at the probe.

12. The apparatus according to claim 10, wherein the acoustic detector comprises an acoustic sensor, which is integrated in or at a wafer chuck on which the semiconductor wafer is mounted.

13. The apparatus according to claim 10, wherein the semiconductor wafer comprises a semiconductor substrate and a stack of connecting layers arranged on the semiconductor substrate and wherein the crack is produced in one of the connecting layers.

14. The apparatus according to claim 10, wherein the acoustic detector comprises a piezoelectric sensor.

15. The apparatus according to claim 10, wherein the apparatus is implemented to contact the probe with the connecting pad to perform an electrical test of the electrical device.

16. The apparatus according to claim 15, wherein the apparatus is implemented to change a probing parameter when the crack is detected, wherein a probing parameter specifies how the probe is contacted with the connecting pad, or to stop a probing process when the crack is detected.

17. An apparatus for detecting a crack in a semiconductor wafer comprising an electrical device and a connecting pad electrically coupled with the electrical device, the apparatus comprising:

a probe adapted to contact the connecting pad; and an acoustic detector adapted to be acoustically coupled to the semiconductor wafer, wherein the acoustic detector is adapted to detect the crack, wherein the semiconductor wafer comprises a semiconductor substrate and a stack of connecting layers arranged on the semiconductor substrate and wherein the crack is produced in one of the connecting layers, wherein a connecting layer of the stack of connecting layers comprises a metal layer and a dielectric layer for electrically insulating the metal layer from a further metal layer of a further connecting layer of the stack of connecting layers, and wherein the crack is produced in the dielectric layer.

18. An apparatus for detecting a crack in a semiconductor wafer comprising an electrical device and a connecting pad electrically coupled with the electrical device, the apparatus comprising:

a probe adapted to contact the connecting pad; and an acoustic detector adapted to be acoustically coupled to the semiconductor wafer, wherein the acoustic detector is adapted to detect the crack, wherein the acoustic detector comprises a plurality of acoustic sensors, which are each acoustically coupled to the semiconductor wafer when the probe is in contact with the connecting pad, and which are adapted to receive a crack signal generated during and due to the generation of the crack, and wherein the acoustic detector is adapted to determine a lateral position of the crack based on the crack signal received by the plurality of acoustic sensors.

19. The apparatus according to claim 18, wherein the semiconductor wafer comprises a plurality of integrated circuit dies, and wherein the apparatus is further adapted to determine based on the lateral position of the crack a defective integrated circuit die of the plurality of integrated circuit dies, which comprises the crack, and to treat the defective integrated circuit die different than other integrated circuit dies, which do not comprise a crack.

20. A method for detecting a crack in a semiconductor wafer comprising an electrical device and a connecting pad electrically coupled with the electrical device, the method comprising:

detecting the crack using an acoustic detector that is acoustically coupled to the semiconductor wafer during contacting the connecting pad with a probe, wherein the method comprises electrically and mechanically contacting the probe with the connecting pad during which the detection of the crack is performed, and performing an electrical and functional test on the electrical device via the probe and the connecting pad.

21. A method for detecting a crack in a semiconductor wafer comprising an electrical device and a connecting pad electrically coupled with the electrical device, the method comprising:

detecting the crack using an acoustic detector that is acoustically coupled to the semiconductor wafer during contacting the connecting pad with a probe, wherein contacting the connecting pad with the probe involves application of a mechanical stress to the semiconductor wafer at the connecting pad.

22. An apparatus for detecting a crack in a semiconductor wafer comprising an electrical device and a connecting pad electrically coupled with the electrical device, the apparatus comprising:
   a probe adapted to contact the connecting pad; and
   an acoustic detector adapted to be acoustically coupled to the semiconductor wafer, wherein the acoustic detector is adapted to detect the crack, wherein the acoustic detector is adapted to detect the crack at the time the probe contacts the connecting pad, and wherein the probe is configured to apply a mechanical stress to the semiconductor wafer at the connecting pad.

23. A apparatus for detecting a crack in a semiconductor wafer comprising an electrical device and a connecting pad electrically coupled with the electrical device, the apparatus comprising:
   a probe adapted to contact the connecting pad; and
   an acoustic detector adapted to be acoustically coupled to the semiconductor wafer, wherein the acoustic detector is adapted to detect the crack, wherein the apparatus is implemented to contact the probe with the connecting pad to perform an electrical test of the electrical device, wherein the apparatus is implemented to change a probing parameter when the crack is detected, the probing parameter involving at least one of a group consisting of a diameter of a cone end of the probe, a parking position of the probe, probing positions of the probe and a speed of the probe with which the probe is moved between the probing positions.

* * * * *